US00PP31733P2

(12) United States Plant Patent
Geibel

(10) Patent No.: US PP31,733 P2
(45) Date of Patent: May 5, 2020

(54) ***PELARGONIUM* PLANT NAMED 'REGBERO'**

(50) Latin Name: *Pelargonium grandiflorum*
Varietal Denomination: Regbero

(71) Applicant: Martin Geibel, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 0 days.

(21) Appl. No.: 16/350,808

(22) Filed: Jan. 15, 2019

(51) Int. Cl.
*A01H 5/02* (2018.01)
*A01H 6/42* (2018.01)

(52) U.S. Cl.
USPC ..... Plt./331
CPC ..... *A01H 6/425* (2018.05)

(58) Field of Classification Search
USPC ..... Plt./331
See application file for complete search history.

*Primary Examiner* — Anne Marie Grunberg
(74) *Attorney, Agent, or Firm* — C. A. Whealy

(57) ABSTRACT

A new and distinct cultivar of Regal Geranium plant named 'Regbero', characterized by its upright, outwardly spreading and uniformly mounded plant habit; moderately vigorous to vigorous growth habit; freely basal branching habit; early and freely flowering habit; red purple and white bi-colored flowers; and no required cooling treatment for flower development.

1 Drawing Sheet

Botanical designation: *Pelargonium grandiflorum.*
Cultivar denomination: 'REGBERO'.

BACKGROUND OF THE INVENTION

The present invention relates to a new and distinct cultivar of Regal Geranium plant, botanically known as *Pelargonium grandiflorum*, and hereinafter referred to by the name 'Regbero'.

The new Regal Geranium plant is a product of a planned breeding program conducted by the Inventor in Dresden, Germany. The objective of the breeding program is to develop new early flowering Regal Geranium plants that do not require a cooling treatment for flower development.

The new Regal Geranium plant originated from a cross-pollination made by the Inventor of two unidentified proprietary selections of *Pelargonium grandiflorum*, not patented, during the summer of 2011. Seed was collected from a number of potential parent plants, combined and sown. The new Regal Geranium plant was discovered and selected by the Inventor as a single flowering plant from within the progeny of the stated mass cross-pollination in a controlled greenhouse environment in Dresden, Germany during the spring of 2014.

Asexual reproduction of the new Regal Geranium plant by vegetative terminal cuttings in a controlled greenhouse environment in Dresden, Germany since October, 2014 has shown that the unique features of this new Regal Geranium plant are stable and reproduced true to type in successive generations.

SUMMARY OF THE INVENTION

Plants of the new Regal Geranium have not been observed under all possible combinations of environmental conditions and cultural practices. The phenotype may vary somewhat with various environmental conditions such as temperature and light intensity without, however, any variance in genotype.

The following traits have been repeatedly observed and are determined to be the unique characteristics of 'Regbero'. These characteristics in combination distinguish 'Regbero' as a new and distinct Regal Geranium plant:

1. Upright, outwardly spreading and uniformly mounded plant habit.
2. Moderately vigorous to vigorous growth habit.
3. Freely basal branching habit.
4. Early and freely flowering habit.
5. Red purple and white bi-colored flowers.
6. No required cooling treatment for flower development.

Plants of the new Regal Geranium can be compared to plants of the *Pelargonium grandiflorum* 'Regbepi', disclosed in U.S. Plant Pat. No. 26,633. In side-by-side comparisons, plants of the new Regal Geranium differ from plants of 'Regbepi' in the following characteristics:

1. Plants of the new Regal Geranium are larger and more vigorous than plants of 'Regbepi'.
2. Plants of the new Regal Geranium are more freely branching than plants of 'Regbepi'.
3. Leaves of plants of the new Regal Geranium are larger than leaves of plants of 'Regbepi'.
4. Plants of the new Regal Geranium are more freely flowering than plants of 'Regbepi'.
5. Plants of the new Regal Geranium flower earlier than plants of 'Regbepi'.

BRIEF DESCRIPTION OF THE PHOTOGRAPH

The accompanying colored photograph illustrates the overall appearance of the new Regal Geranium plant showing the colors as true as it is reasonably possible to obtain in colored reproductions of this type. Colors in the photograph may differ slightly from the color values cited in the detailed botanical description which accurately describe the colors of the new Regal Geranium plant. The photograph comprises a side perspective view of a typical flowering plant of 'Regbero' grown in a container.

DETAILED BOTANICAL DESCRIPTION

The aforementioned photograph and following observations, measurements and values describe plants grown during the winter, spring and summer in 19-cm containers in a glass-covered greenhouse in Dresden, Germany and under cultural practices typical of commercial Regal Geranium production. During the production of the plants, day temperatures averaged 18° C., night temperatures averaged 16° C. and light levels ranged from 15 kilolux to 100 kilolux. Plants were five months old when the photograph was taken and nine months old when the description was taken. In the detailed description, color references are made to The Royal Horticultural Society Colour Chart, 1995 Edition, except where general terms of ordinary dictionary significance are used.

Botanical classification: *Pelargonium grandiflorum* 'Regbero'.

Parentage:

*Female, or seed, parent*.—Unidentified proprietary selection of *Pelargonium grandiflorum*, not patented.

*Male or pollen parent*.—Unidentified proprietary selection of *Pelargonium grandiflorum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Medium in height; upright, outwardly spreading and uniformly mounded plant habit; broad inverted triangle; densely foliated; moderately vigorous to vigorous growth habit; medium growth rate; freely basal branching habit with about 40 lateral branches developing per plant.

*Plant height, to top of umbels*.—About 34 cm.

*Plant height, to top of leaves*.—About 30 cm.

*Plant width*.—About 45 cm.

*Lateral branches*.—Length: About 22 cm. Diameter: About 5 mm. Internode length: About 1.5 cm. Texture: Moderately pubescent. Color: Close to 144A.

Leaf description:

*Arrangement*.—Alternate; simple.

*Length*.—About 4.1 cm.

*Width*.—About 5.3 cm.

*Shape*.—Cordate; palmately lobed.

*Apex*.—Acute.

*Base*.—Cordate, open.

*Margin*.—Serrate.

*Venation pattern*.—Palmate.

*Texture, upper and lower surfaces*.—Sparsely pubescent; leathery.

*Color*.—Developing and fully expanded leaves, upper surface: Close to 137A; venation, close to 137A. Developing and fully expanded leaves, lower surface: Close to 147B; venation, close to 146C. Zonation pattern: None discernible.

*Petioles*.—Length: About 5 cm. Diameter: About 2 mm. Texture, upper and lower surfaces: Sparsely pubescent. Color, upper and lower surfaces: Close to 144A.

Flower description:

*Flower arrangement and flowering habit*.—Single rotate flowers arranged in inversely conical umbels arising from apical leaf axils; umbels displayed above the foliar plane on strong peduncles; flowers face mostly upright to outwardly; freely flowering habit; about four flowers per umbel and about 40 umbels per plant.

*Fragrance*.—None detected.

*Flowering season*.—Early flowering habit, plants begin flowering about five months after planting; in outdoor gardens in Germany, plants flower during the spring and summer; plants do not require a cooling treatment for flower initiation and development, however a cooling period of eight weeks at 9° C. will enhance overall plant quality.

*Flower longevity*.—Flowers last about two weeks on the plant; flowers not persistent.

*Umbel height*.—About 5.5 cm.

*Umbel diameter*.—About 7.5 cm.

*Flower diameter*.—About 4 cm.

*Flower depth (height)*.—About 2.5 cm.

*Flower buds*.—Length: About 1.2 cm. Diameter: About 5 mm. Shape: Spindle-shaped. Color: Close to 146B.

*Petals*.—Quantity per flower: Five arranged in a single whorl; petals imbricate. Length, upper petals: About 2.9 cm. Length, lower petals: About 2.9 cm. Width, upper petals: About 2.3 cm. Width, lower petals: About 1.8 cm. Shape, all petals: Obovate. Apex, all petals: Rounded. Base, all petals: Cuneate. Margin, all petals: Entire; strongly undulate. Texture, all petals, upper and lower surfaces: Smooth, glabrous; velvety. Color, all petals: When opening and fully opened, upper surface: Distally, close to 66C; proximally, close to 155D; venation, close to 66C and 155D; distally, becoming closer to 66D with development. When opening and fully opened, lower surface: Distally, close to 75B; proximally, close to 155D; venation, close to 75B and 155D; color does not change with development.

*Sepals*.—Quantity per flower: Five or six, arranged in a single whorl. Length: About 1.3 cm. Width: About 5 mm. Shape: Lanceolate. Apex: Acute. Margin: Entire. Texture, upper and lower surfaces: Pubescent. Color, upper and lower surfaces: Close to 146B.

*Peduncle (umbel stem)*.—Length: About 5 cm. Diameter: About 2 mm. Strength: Strong, flexible. Angle: Slightly outwardly slanted. Texture: Moderately pubescent. Color: Close to 146B.

*Pedicel (individual flower stem)*.—Length: About 2.5 cm. Diameter: About 1 mm. Strength: Strong; flexible. Angle: Slightly outwardly slanted. Texture: Moderately pubescent. Color: Close to 146B.

*Reproductive organs*.—Androecium: Stamen quantity per flower: About nine. Anther length: About 2 mm. Anther shape: Tubular. Anther color: Close to 77A. Pollen amount: Abundant. Pollen color: Close to 167A. Gynoecium: Pistil quantity per flower: One. Pistil length: About 1.8 cm. Stigma shape: Five or six-parted. Stigma color: Close to 61A. Style length: About 1 cm. Style color: Close to 61B. Ovary color: Close to 147C. Seeds and fruits: To date, seed and fruit development have not been observed on plants of the new Regal Geranium.

Pathogen & pest resistance: To date, plants of the new Regal Geranium have not been observed to be resistant to pathogens and pests common to Regal Geranium plants.

Temperature tolerance: Plants of the new Regal Geranium have been observed to tolerate temperatures ranging from about 1° C. to about 35° C. to 40° C.

It is claimed:

1. A new and distinct Regal Geranium plant named 'Regbero' as illustrated and described.

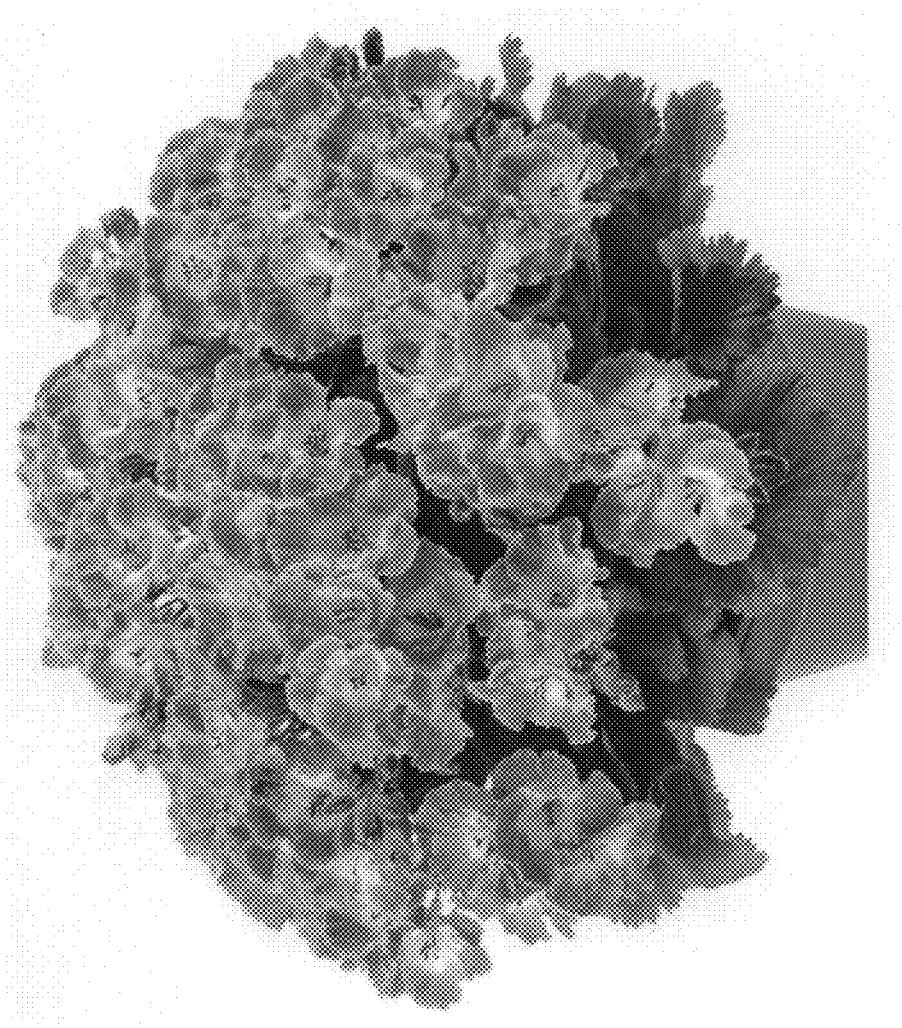

* * * * *